(12) United States Patent
Pace et al.

(10) Patent No.: US 12,012,451 B2
(45) Date of Patent: Jun. 18, 2024

(54) ENGINEERING PH-DEPENDENT ANTIGEN BINDING ACTIVITY INTO ANTI-HIV ANTIBODIES WITH IMPROVED PHARMACOKINETICS

(71) Applicant: The Rockefeller University, New York, NY (US)

(72) Inventors: Craig Stuart Pace, Pacifica, CA (US); David D. Ho, New York, NY (US)

(73) Assignee: The Rockefeller University, New York, NY (US)

( * ) Notice: Subject to any disclaimer, the term of this patent is extended or adjusted under 35 U.S.C. 154(b) by 462 days.

(21) Appl. No.: 16/997,547

(22) Filed: Aug. 19, 2020

(65) Prior Publication Data
US 2021/0054054 A1 Feb. 25, 2021

Related U.S. Application Data

(60) Provisional application No. 62/888,840, filed on Aug. 19, 2019.

(51) Int. Cl.
| | |
|---|---|
| *C07K 16/28* | (2006.01) |
| *A61K 47/68* | (2017.01) |
| *C07K 16/10* | (2006.01) |
| *C12N 15/113* | (2010.01) |

(52) U.S. Cl.
CPC ...... *C07K 16/2812* (2013.01); *A61K 47/6839* (2017.08); *C07K 16/1045* (2013.01); *C07K 2317/41* (2013.01); *C07K 2317/565* (2013.01); *C07K 2317/76* (2013.01); *C07K 2317/94* (2013.01); *C12N 15/1132* (2013.01)

(58) Field of Classification Search
CPC .................................................. C07K 16/2812
See application file for complete search history.

(56) References Cited

U.S. PATENT DOCUMENTS

| | | | | |
|---|---|---|---|---|
| 5,871,732 A | * | 2/1999 | Burkly | A61P 31/18 530/387.3 |
| 9,683,041 B2 | | 6/2017 | Spee et al. | |
| 9,790,276 B2 | * | 10/2017 | Song | A61P 31/18 |
| 2011/0111406 A1 | * | 5/2011 | Igawa | A61P 37/00 435/69.6 |
| 2015/0166662 A1 | | 6/2015 | Song et al. | |

OTHER PUBLICATIONS

Dondelinger, M., et al., Oct. 2018, Understanding the Significance and Implications of Antibody Numbering and Antigen-Binding Surface/Residue Definition, Front. Immunol. 9:Article 2278, pp. 1-15.*
Li, L., et al., 2019, AbRSA: A robust tool for antibody numbering, Prot. Sci. 28:1524-1531.*
International Search Report and Written Opinion for International Application No. PCT/US2020/046966, mailed Jan. 21, 2021 (15 pages).
International Preliminary Report on Patentability for International Patent Application No. PCT/US2020/046966 issued Feb. 17, 2022 (6 pages).

* cited by examiner

*Primary Examiner* — Jeffrey S Parkin
(74) *Attorney, Agent, or Firm* — Clark & Elbing LLP (57) ABSTRACT

The disclosure is directed to a histidine-mutated anti-HIV antibody having one or more mutations at the residue Y53a, D58, K96, D97, N98, or T100a in the heavy chain of ibalizumab, and at the residue S26, L30, L33, Q89, Y92, S93 or Y94 in the light chain of ibalizumab. In addition, the disclosure also is directed to two histidine mutated variants with two mutations, one with mutations at the residues Y53a and Y94, and the other with mutations at the residues D58 and L30 in the heavy and light chains of ibalizumab, respectively.

16 Claims, 6 Drawing Sheets
(6 of 6 Drawing Sheet(s) Filed in Color)
Specification includes a Sequence Listing.

ENGINEERING PH-DEPENDENT ANTIGEN BINDING ACTIVITY INTO ANTI-HIV ANTIBODIES WITH IMPROVED PHARMACOKINETICS

SEQUENCE LISTING

The instant application contains a Sequence Listing which has been submitted electronically in ASCII format and is hereby incorporated by reference in its entirety. Said ASCII copy, created on Aug. 19, 2020, is named 50538-033002_Sequence_Listing_08.19.20_ST25 and is 12,398 bytes in size.

CROSS-REFERENCE TO RELATED APPLICATIONS

The application claims priority to U.S. Provisional Application No. 62/888,840, filed on Aug. 19, 2019, the contents of which is hereby incorporated herein by reference in its entirety.

FIELD OF THE INVENTION

This disclosure generally relates to improved anti-HIV antibodies for HIV prevention and treatment. This disclosure also generally relates to histidine mutation of anti-HIV antibodies. In particular, this disclosure relates to histidine-mutated anti-HIV antibodies for HIV prevention and therapy.

BACKGROUND OF THE INVENTION

HIV-1 entry is triggered by interaction of the viral envelope (Env) glycoprotein gp120 with domain 1 (D1) of the T-cell receptor CD4. Ibalizumab (iMab) is a potent and broadly HIV-1 neutralizing Ab (Jacobson et al., *Antimicrob. Agents Chemother.* 53:450-457, 2009; Kuritzkes et al., *J. Infect. Dis.* 189:286-291, 2004; both of which are hereby incorporated by reference in their entirety), which neutralizes HIV by binding mainly to domain 2 (D2) of the CD4 receptor on host T-cells, thus blocking the ability of HIV to use these CD4 receptors to gain entry into T-cells and produce infection (Burkly et al., *J. Immunol.* 149:1779-178, 1992). In a large panel of primary isolates (118 Env pseudo-typed viruses) tested recently, ibalizumab neutralized 92% of all viruses as defined by 50% inhibition of infection, and 47.4% of viruses as defined by 90% inhibition of infection. While ibalizumab can potently inhibit a broad range of HIV isolates, a significant fraction of HIV variants can still escape the inhibitory activity of ibalizumab. It has been reported recently that loss of asparagine-linked glycosylation sites in the variable region 5 of HIV type 1 envelope is associated with resistance to ibalizumab (Toma et al., *J. Virology* 85(8): 3872-2880, 2011; Pace et al., *J. Acquir. Immune Defic. Syndr.* Epub ahead of print: September 2012).

Antibodies are glycosylated at conserved positions in their constant regions, and the presence and structure of the carbohydrate attached to the constant region can affect antibody activity (see review by Wright and Morrison, *TIBTECH* 15: 26-32, 1997).

It was reported that the introduction of an N-linked carbohydrate in the heavy chain, not the light chain, resulted in improved solubility (Pepinsky et al., *Protein Sci* 19, 954-966, 2010; Wu, et al., *Protein Eng Des Sel* 23, 643-651, 2010). In Pepinsky, the modification was at the constant region, not the variable region. However, none of previous studies provides the effect of a glycan strategically placed in the variable region of an antibody.

It has been reported that loss of asparagine-linked glycosylation sites in the variable region 5 of HIV type 1 envelope is associated with resistance to ibalizumab (Toma et al., *J. Virology* 85(8): 3872-2880, 2011; Pace et al., *J. Acquir. Immune Defic. Syndr.* Epub ahead of print: September 2012). Further, it has been disclosed in U.S. Pat. Nos. 9,790,276B2 and 9,587,022B2 that glycan-modified anti-CD4 monoclonal antibodies provided the enhanced activity through glycan modification in the variable regions of the anti-CD4 antibodies. In these patents, the glycan-modified anti-CD4 antibody is a modified form of an anti-CD4 antibody having an engineered N-linked glycosylation site in its variable region. In some specific embodiments, the engineered N-linked glycosylation site is located at an amino acid position of the light chain of ibalizumab selected from the group consisting of residues 30E Gln, 52Ser, 53Thr, 54Arg, 60Asp, 65Ser, 67Ser, and 76Ser. In one particular example, the glycosylation site is one of 30E Gln, 52Ser, 53Thr, 54Arg, 65Ser, 67Ser and combination thereof, which provides an improved activity for HIV prevention and treatment.

It is still desirable to develop further improved anti-HIV antibodies for HIV prevention and therapy.

SUMMARY OF THE INVENTION

The present invention provides a new approach for enhancing the activity of an anti-HIV antibody through histidine-mutation in the variable region of the light or heavy chain of said antibody. The numbering for ibalizumab follows the Kabat and Chothia Numbering Scheme.

In one aspect, the present invention provides a histidine-mutated anti-HIV antibody having one or more mutations at the residue(s) in the heavy chain of said antibody, wherein the residue(s) is(are) selected from the group consisting of Y53a, D58, K96, D97, N98, T100a and combination thereof, wherein the anti-HIV antibody is a glycan-modified anti-CD4 monoclonal antibody as disclosed in U.S. Pat. Nos. 9,790,276B2 and 9,587,022B2, which are incorporated herein by reference in their entirety.

In another aspect, the present invention provides a histidine-mutated anti-HIV antibody having one or more mutations at the residue(s) in the light chain of said antibody, wherein the residue(s) is(are) selected from the group consisting of S26, L30, L33, Q89, Y92, S93, Y94 and combination thereof.

In one further aspect, the present invention provides a histidine-mutated anti-HIV antibody having a combination of the mutation at one of the above mentioned residues in the heavy chain, and the mutation at one of the above mentioned residues in the light chain of said antibody.

In one yet aspect, the present invention provides a histidine-mutated anti-HIV antibody having a combination of the mutation at the residue Y53a in the heavy chain, and the mutation at one of the above mentioned residues in the light chain of said antibody.

In one yet aspect, the present invention provides a histidine-mutated anti-HIV antibody having a combination of the mutation at the residue D58 in the heavy chain, and the mutation at one of the above mentioned residues in the light chain of said antibody In one embodiment of the invention, the anti-HIV antibody is an anti-CD4 antibody, in particular ibalizumab with glycan-modifications as disclosed in U.S. Pat. Nos. 9,790,276B2 and 9,587,022B2.

In one example, the present invention provides an engineering variant, which is a variant with two histidine-mutations at the residues Y53a in the heavy chain, and Y94 in the light chain of ibalizumab, respectively (called as "HC Y53a/LC Y94" or Y53a/Y94" or "Y94/Y53a"). The variant HC Y53a/LC Y94 displays the desired antibody-antigen binding properties at different pH values with in vitro HIV-1 neutralization activity equivalent to the wild type of ibalizumab ("wt"), indicating that these mutations did not interfere with normal ibalizumab function. The variant HC Y53a/LC Y94 has a 2.1-fold longer half-life than the wild type ibalizumab in Rhesus macaques (P=0.008) that resulted in 50% longer CD4 receptor occupancy. If similar improvements in half-life and receptor occupancy was observed in humans, the variant HC Y53a/LC Y94 requires less frequent dosing than the wild type ibalizumab.

In another example, the present invention provides an engineering variant, which is a variant with two histidine mutations at D58 in the heavy chain, and L30 in the light chain of ibalizumab, respectively (called as "HC D58/LC L30" or "F58/L30" or "L30/D58").

BRIEF DESCRIPTION OF THE DRAWINGS

The application file contains drawings executed in color. Copies of this patent or patent application with the color drawings will be provided by the office upon request and payment of the necessary fee.

DETAILED DESCRIPTION OF THE INVENTION

The above-mentioned and other features of this invention and the manner of obtaining and using them will become more apparent, and will be best understood, by reference to the following description.

Unless otherwise defined herein, scientific and technical terms used herein have the meanings that are commonly understood by those of ordinary skill in the art.

The present invention has demonstrated for the first time that the function of a monoclonal antibody can be improved through glycan modification in the variable region of anti-HIV antibody and the histidine-modification in the heavy chain.

Accordingly, the present invention provides a histidine-modified anti-HIV antibody having one or more mutations at the residue in the heavy chain of said antibody selected from the group consisting of Y53a, D58, K96, D97, N98, T100a and combination thereof; wherein the anti-HIV antibody is a glycan-modified anti-CD4 monoclonal antibody as disclosed in U.S. Pat. Nos. 9,790,276B2 and 9,587,022B2.

In addition, the present invention provides a histidine-modified anti-HIV antibody having one or more mutations at the residue in the light chain of said antibody selected from the group consisting of S26, L30, L33, Q89, Y92, S93, Y94 and combination thereof.

The present invention also provides a histidine-modified anti-HIV antibody having a combination of the mutation at one of the above mentioned residues in the heavy chain, and the mutation at one of the above mentioned residues in the light chain of said antibody.

In one example, the present invention provides a histidine-modified anti-HIV antibody having a combination of the mutation at the residue Y53a or D58 in the heavy chain, and the mutation at the above mentioned residues in the light chain of said antibody In one particular example, the present invention provides an engineering variant HC Y53a/LC Y94, and HC D58/LC L30 displaying the desired antibody-antigen binding properties at different pH values with in vitro HIV-1 neutralization activity equivalent to wt, indicating that these mutations did not interfere with normal ibalizumab function.

Definitions

An "antigen" refers to a molecule which contains one or more epitopes and which is capable of eliciting an immunological response. "Antigenic molecules" are also used in a general sense to refer to molecules that are binding targets of the glycan modified proteins disclosed herein.

An "epitope", also known as antigenic determinant, is the portion of an antigenic molecule or molecules that is recognized by the immune system, i.e., B cells, T cells or antibodies. An epitope can be a conformational epitope or a linear epitope. A conformational epitope is formed by discontinuous sections of an antigenic molecule, or formed by multiple molecules. In the case where the antigen is a protein, a conformational epitope can be formed by discontinuous amino acid residues of the same protein molecule, or by amino acid residues on different molecules of the protein (e.g., a quaternary epitope formed by a multimer of the protein). A linear epitope is formed by continuous sections of an antigen, e.g., a continuous sequence of amino acids of a protein antigen.

The term "antibody" is used herein broadly and encompasses intact antibody molecules, which include intact polyclonal, monoclonal, monospecific, polyspecific, chimeric, humanized, human, primatized, single-chain, single-domain, synthetic and recombinant antibodies, and antibody fragments that have a desired activity or function.

The term "antibody fragments," as used herein, includes particularly antigen-binding fragments of an intact antibody. Examples of antigen-binding fragments include, but are not limited to, Fab fragments (consisting of the VL, VH, CL and CH1 domains), Fab' fragments (which differs from Fab fragments by having an additional few residues at the C-terminus of the CH1 domain including one or more cysteines from the antibody hinge region), $(Fab')_2$ fragments (formed by two Fab' fragments linked by a disulphide bridge at the hinge region), Fd fragments (consisting of the VH and CH1 domains), Fv fragments (referring to a dimer of one heavy and one light chain variable domain in tight, non-covalent association which contains a complete antigen recognition and binding site), dAb fragments (consisting of a VH domain), single domain fragments (VH domain, VL domain, VHH domain, or VNAR domain), isolated CDR regions, scFv (or "single chain Fv", referring to a fusion of the VL and VH domains, linked together via a linker), and other antibody fragments that retain antigen-binding function.

The term "variable region" refers to the antigen-binding region of an antibody, which varies greatly between different antibody molecules. The region of an antibody that does not vary the same way and generally engages effector functions of the immune system is called "constant region". Approximately the first 110 amino acids of an immunoglobulin chain (mature form) constitute its variable domain. The two variable domains of the heavy chain (VH) and the two variable domains of the light chain (VL) make up the variable region of an antibody. The six constant domains of the heavy chain (CH1, CH2, and CH3) and the two constant domains of the light chain (CL) make up the constant region of an antibody.

The term "CDR" or "complementarity determining region" refers to the hypervariable regions within the variable domain of an antibody. There are 3 CDRs in each of the heavy chain and light chain variable domains, and are composed of amino acid residues responsible for antigen-binding. The term "framework region" or "FR" refers to the more conserved portions of the variable domains and is composed of residues other than the hypervariable region residues.

The term "antigen-binding site" of an antibody means a conformation and/or configuration formed by amino acids of the antibody to which an antigen binds. For example, the three CDRs of each of the VH and VL domains interact to define an antigen-binding site on the surface of the VH-VL dimer. Together, the six CDRs confer antigen-binding specificity to the antibody. It should be noted, however, a single variable domain (i.e., VH or VL) can also recognize and bind antigen, albeit often less effectively than the whole binding site with all six CDRs.

The term "chimeric antibody" refers to antibodies containing polypeptides from different sources, e.g., different species or different antibody class or subclass. Examples of chimeric antibodies include an antigen-binding portion of a murine monoclonal antibody fused an Fc fragment of a human immunoglobulin. Methods for making chimeric antibodies are known in the art; for example, methods described in patents by U.S. Pat. No. 4,816,397 to Boss et al. and U.S. Pat. No. 4,816,567 to Cabilly et al.

The term "humanized antibody" refers to antibodies that contain non-human sequence elements in a human immunoglobulin backbone or framework. Generally, humanized antibodies are human immunoglobulins (recipient antibody) in which residues from a hypervariable region (CDRs) of the recipient are replaced by residues from a hypervariable region of a non-human species (donor antibody) such as mouse, RAT, rabbit or nonhuman primate having a desired specificity, affinity and capacity. In some instances, framework region (FR) residues of the human immunoglobulin are also replaced by non-human residues. Humanized antibodies may also, in some instances, contain residues that are not found in either the recipient antibody or the donor antibody and introduced to further refine antibody performance. In general, a humanized antibody contains substantially all of at least one, and typically two, variable domains, in which all or substantially all of the hypervariable regions correspond to those of a non-human immunoglobulin and all or substantially all of the framework regions are those of a human immunoglobulin sequence. A humanized antibody optionally also contains at least a portion of an immunoglobulin constant region (Fc), typically that of a human immunoglobulin. Methods for making humanized antibodies are documented in the art; see, for example, by U.S. Pat. No. 5,225,539 to Winter and U.S. Pat. No. 4,816,397 to Boss et al.

The term "non-human primatized antibody" refers to antibodies that contain human sequence elements or non-primate sequence elements in a non-human primate immunoglobulin backbone or framework. For example, non-human primatized antibodies can be made from a non-human primate immunoglobulin (recipient antibody) by replacing residues in a hypervariable region (CDRs) of the recipient antibody with residues from a hypervariable region of a donor antibody from a human or non-primate species such as mouse, RAT or rabbit having a desired specificity, affinity and capacity. Alternatively, non-human primatized antibodies can be made suitable for administration to a desirable primate species by using a recipient immunoglobulin having human or non-primate sequences or sequences from a different primate species and introducing the Fc fragment, and/or residues, including particularly framework region residues, from the desirable primate, into the recipient immunoglobulin. Examples of non-human primatized antibodies include "monkeynized" antibodies disclosed herein in the Examples section.

The term "monospecific antibody" refers to antibodies that recognize and bind to one epitope.

The term "polyspecific antibody" refers to antibodies formed from at least two separate antibodies and binding to multiple (i.e., two or more) separate epitopes.

The term "neutralizing antibody" refers to an antibody that inhibits, reduces or completely prevents HIV-1 infection. Whether an antibody is a neutralizing antibody can be determined by in vitro assays described in the Examples section hereinbelow.

The term "potent neutralizing antibody" refers to an antibody which, when used at a low concentration, reduces HIV-1 infection by at least 50%, 60%, 70%, 80%, 90%, 95%, 99% or greater. Concentrations below 50 μg/ml, between 1 and 50 μg/ml, or even below 1 μg/ml, are considered "low concentrations". In some embodiments, low concentrations are concentrations in the picomolar range, such as 10-900 ng/ml, and include any concentration in that range, such as 800, 700, 600, 500, 400, 300, 200, 100, 75, 50, 25, 10 ng/ml, or even less than 10 ng/ml.

The term "broad neutralizing antibody" refers to an antibody which inhibits HIV-1 infection, as defined by a 50% inhibition of infection in vitro, in more than 50%, 60%, 70%, 80%, 90%, 95%, 99% or greater, of a large panel of (greater than 100) HIV-1 envelope pseudotyped viruses and viral isolates; for example, a large panel of isolates representing envelope diversity by geography, clade, tropism, and stage of infection.

The term "fragment" as used herein refers to a physically contiguous portion of the primary structure of a biomolecule. In the case of proteins, a fragment may be defined by a contiguous portion of the amino acid sequence of a protein and may be at least 3-5 amino acids, at least 6-10 amino acids, at least 11-15 amino acids, at least 16-24 amino acids, at least 25-30 amino acids, at least 30-45 amino acids and up to the full length of the protein minus a few amino acids. In the case of polynucleotides, a fragment is defined by a contiguous portion of the nucleic acid sequence of a polynucleotide and may be at least 9-15 nucleotides, at least 15-30 nucleotides, at least 31-45 nucleotides, at least 46-74 nucleotides, at least 75-90 nucleotides, and at least 90-130 nucleotides. In some embodiments, fragments of biomolecules are immunogenic fragments.

A "peptide" is any compound formed by the linkage of two or more amino acids by amide (peptide) bonds, usually a polymer of alpha-amino acids in which the alpha-amino group of each amino acid residue (except the NH2 terminus) is linked to the alpha-carboxyl group of the next residue in a linear chain. The terms peptide, polypeptide and poly (amino acid) are used synonymously herein to refer to this class of compounds without restriction as to size, unless indicated to the contrary. Members of this class having a large size are also referred to as proteins and include antibodies.

Figure 4:
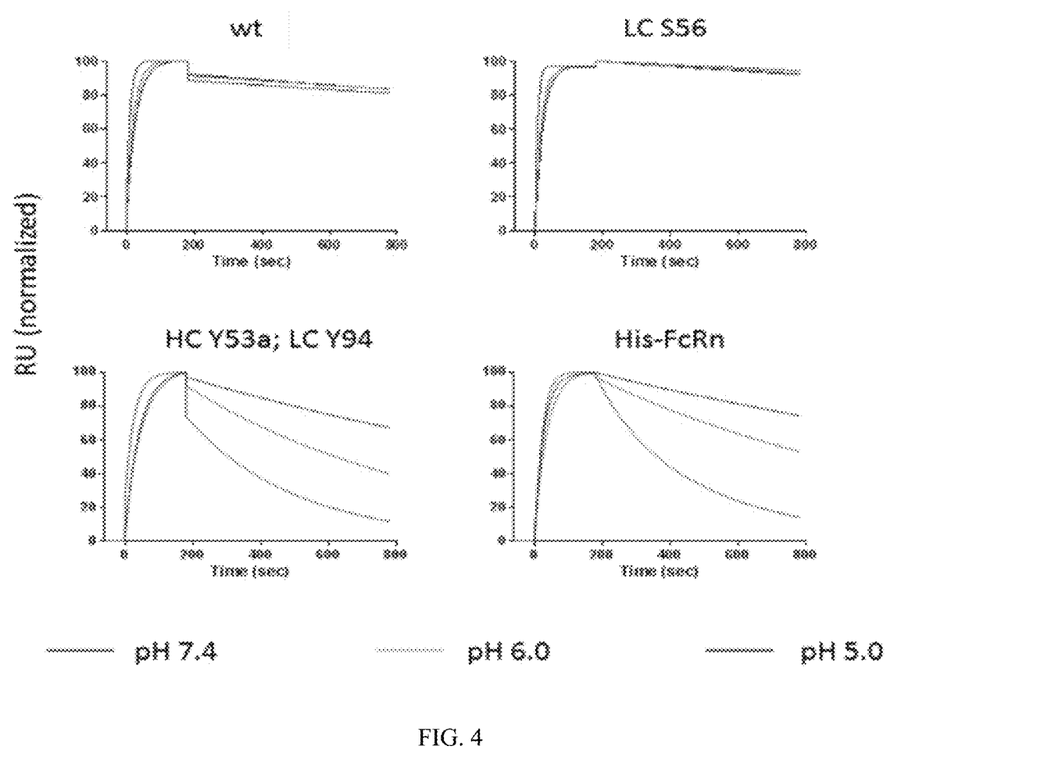
FIG. 4 provides the comparison of the antigen-binding kinetics of the wild type ibalizumab (wt) and the variant HC Y53a/LC Y94 at pH 7.4, pH 6.0 and pH 5.0 as determined by surface plasmon resonance analysis. For HC Y53a; LC94 and His-FcRn, pH7.4 is the top line, pH 6.0 is the middle line and pH5.0 is the bottom line.
Figure 5:
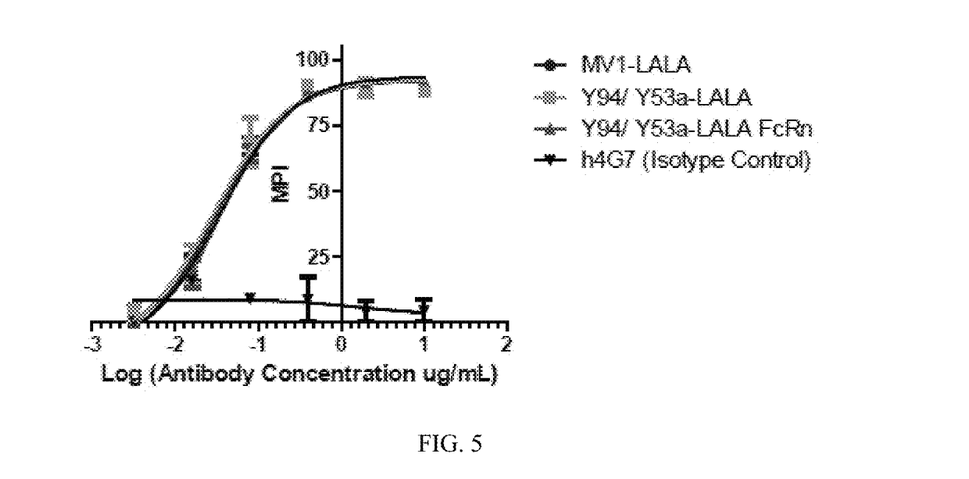
FIG. 5 provides the in vitro HIV-1 neutralization activity of the variant HC Y53a/LC Y94, including Y94/Y53a-LALA and Y94/Y53a-LALA FcRn was similar to that of the wild type ibalizumab (MV1-LALA).
Figure 6A:
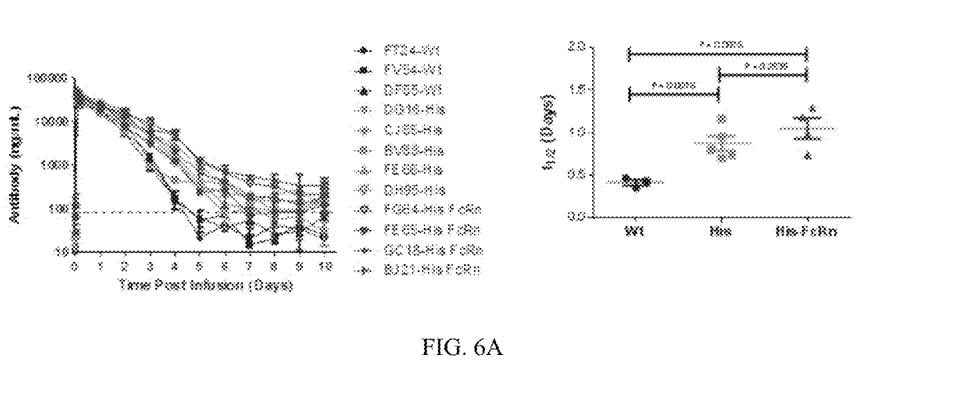
FIG. 6A shows the pharmacokinetics of wild type ibalizumab (Wt, blue lines) and the variant HC Y53a/LC Y94 (marked with "His" presented by green lines and "His FcRn" presented by red lines) in Rhesus macaques administered the respective antibody at 0.75 mg/kg. Each line indicates the antibody concentration observed in an individual rhesus macaque. Dotted line indicates the lower limit of quantification (LLQ) of the assay.
Figure 6B:
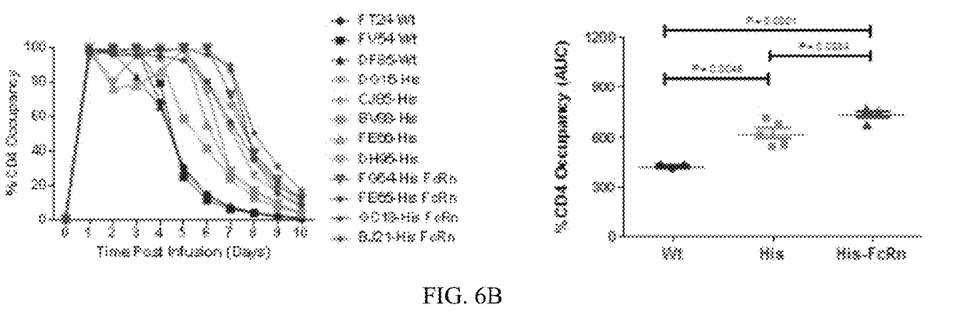
FIG. 6B provides the duration of CD4 occupancy by the wild type ibalizumab (Wt, blue lines) and the variant HC Y53a/LC Y94 (His, green lines and His FcRn, red lines) in Rhesus macaques administered the respective antibody at 0.75 mg/kg. Each line indicates the CD4 occupancy observed in an individual rhesus macaque.

In one particular example of the present invention, one variant, HC Y53a/LC Y94, is confirmed to have the desired antibody-antigen binding properties at different pH's (FIG. 4), with in vitro HIV-1 neutralization activity equivalent to the wild type ibalizumab, indicating that these mutations did not interfere with normal ibalizumab function (FIG. 5). The variant Y53a/LC Y94 has a 2.1-fold longer half-life than the wild type ibalizumab in Rhesus macaques (P=0.008; FIG. 6A) that resulted in 50% longer CD4 receptor occupancy (FIG. 6B). If similar improvements in half-life and receptor occupancy are observed in humans, HC Y53a/LC Y94 should require less frequent dosing than the wild type ibalizumab.

The anti-HIV antibodies have been described in the art and can also be readily generated as the protein sequence of the CD4 receptor is available to those skilled in the art. CD4 has four immunoglobulin domains (D1 to D4) that are located on the extracellular surface of the cell, and uses its D1 domain to interact with the B2-domain of MHC class II molecules. In some embodiments, the anti-HIV antibody may be one anti-CD4 antibody binding to one or more of D1, D1-D2 junction, D2, the BC or FG loop of D2, or any combination thereof. In specific embodiments, the anti-CD4 antibodies used in this disclosure are directed principally to the second immunoglobulin-like domain (D2) (amino acid positions 98-180) of the CD4 receptor. Antibodies directed to the D2 domain of CD4 have the desirable property of blocking HIV infection without interfering with immune functions mediated by interaction of CD4 with the major histocompatibility complex (MHC) class II molecules. In other embodiments, the anti-CD4 antibody used in the present invention binds to an epitope located in the BC-loop of D2 near the D1-D2 junction of the CD4 receptor (amino acids 121-127). In still other embodiments, the anti-CD4 antibody binds to the FG-loop of D2 (amino acids 163-165) and part of D1 (amino acids 77-96). The amino acid numbering corresponds to positions of the mature form of the CD4 receptor, not including the signal peptide. The amino acid sequence of the human CD4 receptor is set forth in SEQ ID NO: 1, in which amino acids 1-25 represent a signal peptide, amino acids 26-122 constitute D1, and amino acids 123-205 constitute D2.

In a specific embodiment, the anti-HIV antibody is a CD4 monoclonal antibody, which may be the humanized antibody, ibalizumab or "iMab" (previously known as TNX-355, or hu5A8). Ibalizumab potently blocks infection by a broad spectrum of HIV-1 isolates and targets an epitope located in the BC-loop of D2 near the D1-D2 junction of the CD4 receptor, without interfering with immune functions mediated by interaction of CD4 with the major histocompatibility complex (MHC) class II molecules. One example of the anti-CD4 antibody is that provided in U.S. Pat. No. 5,871,732, which is entirely incorporated by reference herein.

In another embodiment, the anti-CD4 antibody or fragment thereof is a mutant of ibalizumab with improved stability. One example is the anti-CD4 antibody having one or more substitutions in the hinge region that prevent intrachain disulfide bond formation resulting in antibody molecules with surprisingly improved bivalent stability, for instance, those provided in WO2008134046 (A1), published on Apr. 27, 2007, which is incorporated herein by reference.

According to the embodiments of the invention, the anti-CD4 antibody may be generated by IgG 4 or IgG 1. In one example of the invention, an anti-CD4 IgG 1 antibody with binding affinity to CD4 was prepared, designated as MV1. The MV1 has a leucine to phenylalanine change at position 234, a leucine to glutamic acid change at position 235 and a proline to serine change at position 331 of the IgG 1 constant region. The MV1 has the amino acid sequences for the heavy chain and light chain as set forth in SEQ ID NOS: 2-3, respectively.

In some examples of the invention, the anti-CD4 antibody may comprise one or more modifications in the Fc region or FcRn region of the heavy chain to improve recycling of the anti-CD4 antibody. One particular example is the anti-CD4 antibody comprises an amino acid sequence of heavy chain as set forth in SEQ ID NO: 5.

In a particular example, the anti-CD4 antibody is ibalizumab modified by glycosylation at the amino acid position selected from the group consisting of positions 30E Gln, 52Ser, 53Thr, 54Arg, 60Asp, 65Ser, 67Ser, and 76Ser, as disclosed in U.S. Pat. Nos. 9,790,276B2 and 9,587,022B2. In one preferred example, the glycosylation site at 30E Gln, 52Ser, 53Thr, 54Arg, 65Ser, or 67Ser provides improved activity. In one more preferred example of the invention, the glycosylation site is at position 52Ser.

Based on the findings in the invention, it is indicated that the histidine-mutation approach may be adapted to enhance their functional activity of the anti-HIV antibodies. Using the structural-activity relationship (SAR), it is conceivable that increasing the bulk at key positions on the antibody could lead to improved activity so as to generate a superior antibody product.

Pharmaceutical Composition

Pharmaceutical composition comprising an engineering antibody disclosed herein can be prepared by mixing the antibody with one or more optional pharmaceutically acceptable carriers. Pharmaceutically acceptable carriers include solvents, dispersion media, isotonic agents and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, antioxidants including ascorbic acid and methionine, chelating agents such as EDTA; salt forming counter-ions such as sodium; non-ionic surfactants such as TWEEN™, PLURONICS™ or polyethylene glycol (PEG), or combinations thereof.

The pharmaceutical composition can contain more than one active compound, e.g., one or more antibodies, in combination with one or more additional beneficial compound for inhibiting, preventing and treating HIV infections.

The active ingredients can be combined with the carrier in any convenient and practical manner, e.g., by admixture, solution, suspension, emulsification, encapsulation, absorption and the like, and can be made in formulations such as tablets, capsules, powder (including lyophilized powder), syrup, suspensions that are suitable for injections, ingestions, infusion, or the like. Sustained-release preparations can also be prepared.

Methods of Treatment and Prevention

In a further aspect, the histidine mutated antibodies disclosed herein, optionally provided in pharmaceutically acceptable carrier, are employed for the treatment and prevention of HIV infection in a subject, as well as prevention of HIV transmission.

The term "treatment" of HIV infection refers to effective inhibition of the HIV infection so as to delay the onset, slow down the progression, reduce viral load, and/or ameliorate the symptoms caused by HIV infection.

The term "prevention of HIV infection" means the onset of HIV infection is delayed, and/or the incidence or likelihood of HIV infection is reduced or eliminated.

The term "prevention of HIV transmission" means the incidence or likelihood of HIV being transmitted from one individual to another (e.g., from an HIV-positive woman to the child during pregnancy, labor or delivery, or breastfeeding; or from an HIV-positive subject to an HIV-negative partner) is reduced or eliminated.

The term "subject" refers to any primate subject, including human and non-human subjects (e.g., rhesus subjects).

To inhibit, treat and/or prevent HIV infection, a therapeutically effective amount of a histidine-mutated antibody disclosed herein is administered to a subject in need.

The term "therapeutically effective amount" means the dose required to effect an inhibition of HIV infection so as to treat and/or prevent HIV infection. The dosage of an antibody depends on the disease state and other clinical factors, such as weight and condition of the subject, the subject's response to the therapy, the type of formulations and the route of administration. The precise dosage to be therapeutically effective and non-detrimental can be determined by those skilled in the art. As a general rule, a suitable dose of an antibody for the administration to adult humans parenterally is in the range of about 0.1 to 20 mg/kg of patient body weight per day, once a week, or even once a month, with the typical initial range used being in the range of about 2 to 10 mg/kg. Since the antibodies will eventually be cleared from the bloodstream, re-administration may be required. Alternatively, implantation or injection of antibodies provided in a controlled release matrix can be employed.

The antibodies can be administered to the subject by standard routes, including the oral, transdermal or parenteral (e.g., intravenous, intraperitoneal, intradermal, subcutaneous or intramuscular). In addition, the antibodies can be introduced into the body, by injection or by surgical implantation or attachment such that a significant amount of a desirable antibody is able to enter blood stream in a controlled release fashion.

The invention is further illustrated by the following example, which should not be construed as further limiting.

EXAMPLES

Example 1

Identification of Ibalizumab CDR Residues Capable of Mediating pH-Dependent CD4-Binding Activity To identify pH-dependent antigen-binding ibalizumab variants, we systematically mutated each CDR residue of the ibalizumab VH and VL genes to histidine, expressed and purified each variant and assessed each variants CD4-binding activity relative to wild type at pH 7.4, 6.0 and 5.0 by competition ELISA using HRP-labeled wild type ibalizumab. The goal was to identify ibalizumab histidine variants with the greatest loss of CD4-binding at pH 6.0 relative to CD4 binding at pH 7.4 (pH 6.0/pH 7.4) with the least loss of CD4-binding activity at pH 7.4. While the relevance of pH-dependent CD4-binding activity at pH 5.0 in vivo was unclear, we included a pH 5.0 assessment for improving the identification of histidine variants that mediate pH-dependent CD4-bindingving, especially when assessing the contributions of single residues where their effect on binding affinity was expected to be minor.

Figure 1A:
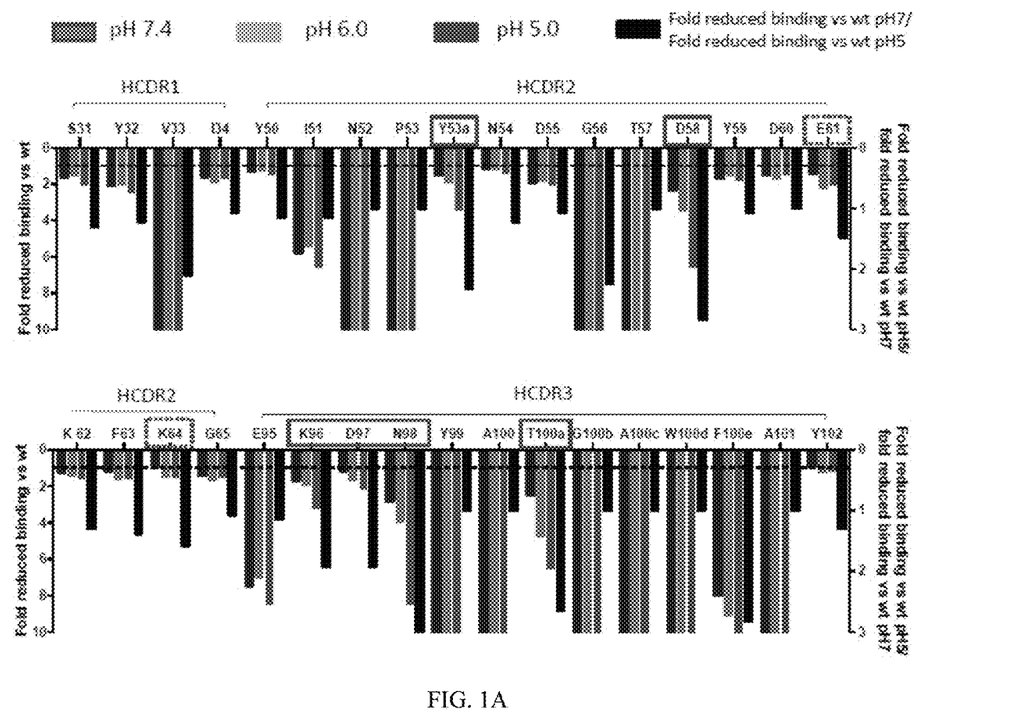
FIG. 1A provides the CD4-binding activity of each of the variants of ibalizumab with a histidine mutation in each of different CDR residues in the heavy chain, relative to the wild type at pH 7.4, 6.0 and 5.0 (left to right at each residue) by competition ELISA. For each residue the rightmost column is "Fold reduced binding vs wt pH 5.0/Fold reduced binding vs wt pH 7.4."
Figure 1B:
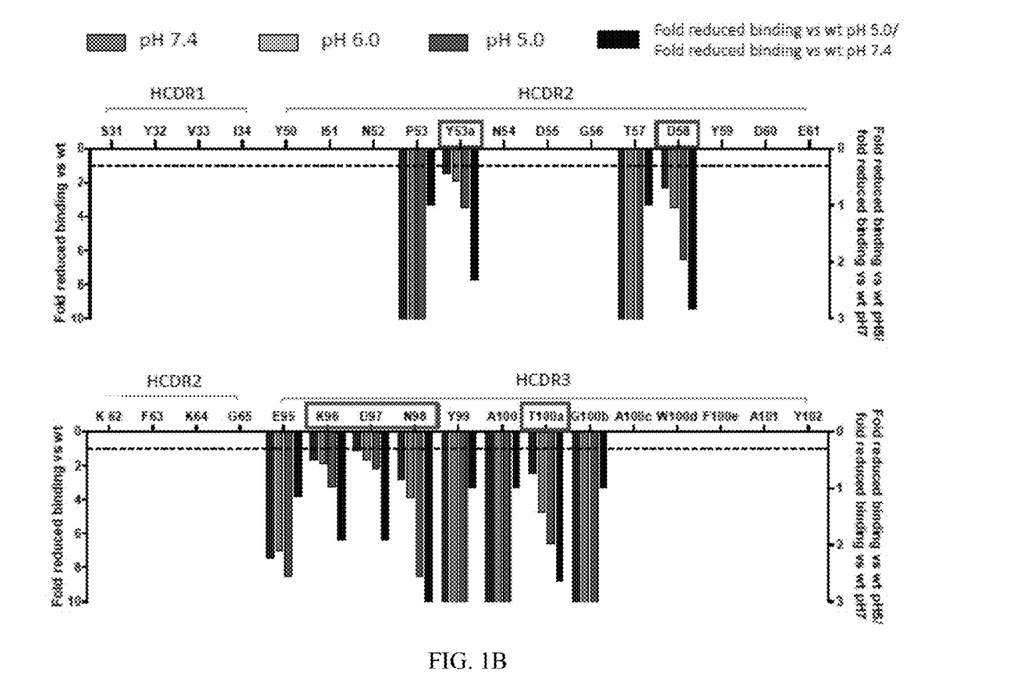
FIG. 1B shows that six variants with a histidine mutation at the residue Y53a, D58, K96, D97, N98 or T100a in the heavy chain of ibalizumab, maintained CD4-binding activity at pH 7.4≤ 3.0-fold as compared to the wild type ibalizumab (pH 7.4, 6.0 and 5.0 (left to right at each residue)). For each residue the rightmost column is "Fold reduced binding vs wt pH 5.0/Fold reduced binding vs wt pH 7.4."

For a residue to be considered pH-dependent, it was evaluated, upon mutation to histidine in ibalizumab, to exhibit consistent pH-dependent loss of ability to compete with the wild type (wt) ibalizumab across the pHs tested, such that the loss of affinity vs wt should be pH 5.0 >6.0>7.4. For the heavy chain, the changes of the CD4-binding activity at pH 5.0, 6.0 and 7.4 with the mutations at different residues ("HCDR His variants") were given in FIG. 1A, and 10 HCDR His variants when mutated to histidine were found to exhibit ≥ 50% less CD4-binding activity at pH 5.0 relative to pH 7.4 (pH 5.0/pH 7.4≥ 1.5). Of these 10 HCDR His variants, only 6 variants with a histidine mutation at the residue: Y53a, D58, K96, D97, N98 or T100a, which maintained CD4-binding activity at pH 7.4≤ 3.0-fold as compared to the wild type, as shown in FIG. 1B.

Figure 2A:
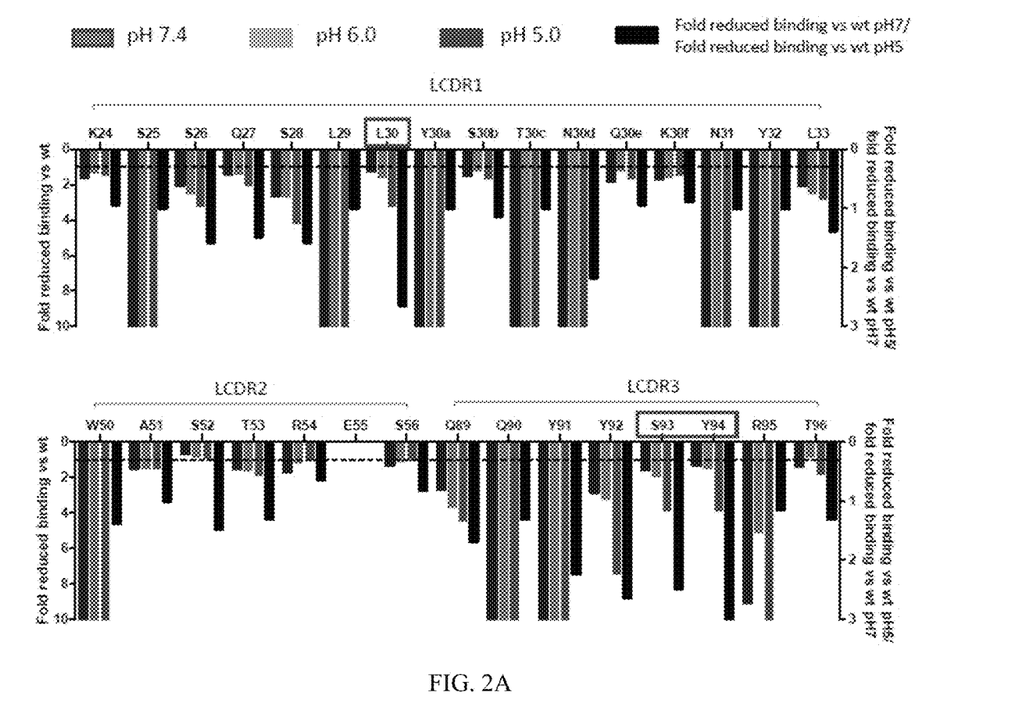
FIG. 2A provides the CD4-binding activity of each of the variants of ibalizumab with a histidine mutation in each of different CDR residues in the light chain, relative to the wild type at pH 7.4, 6.0 and 5.0 (left to right at each residue) by competition ELISA. For each residue the rightmost column is "Fold reduced binding vs wt pH 7/Fold reduced binding vs wt pH 5."
Figure 2B:
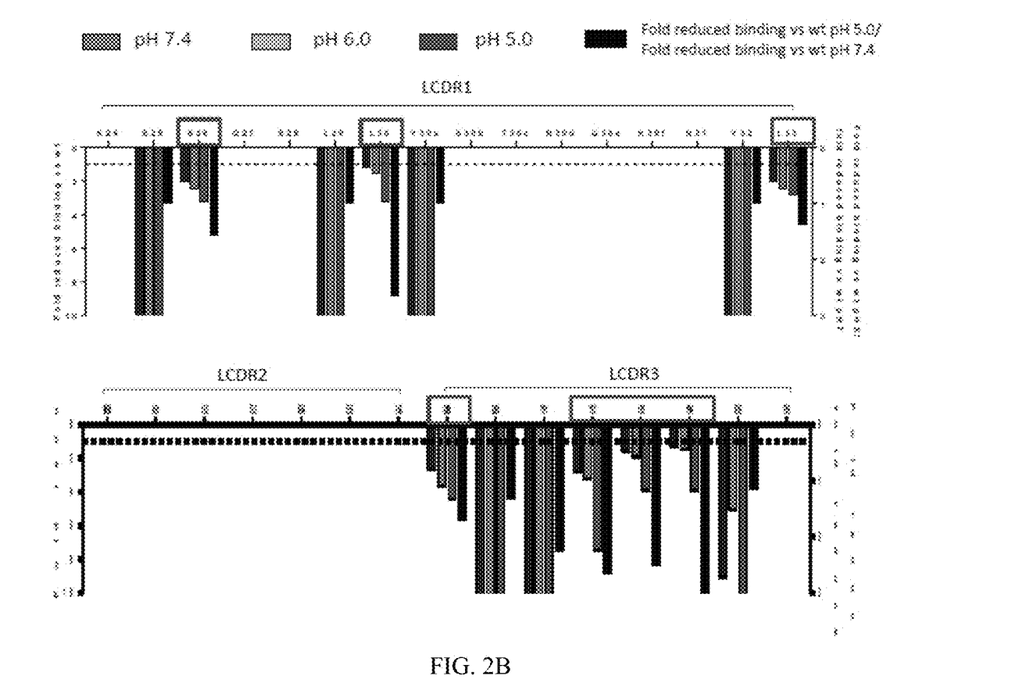
FIG. 2B shows that seven variants with a histidine mutation at the residue S26, L30, L33, Q89, Y92, S93 or Y94 in the light chain of ibalizumab, maintained CD4-binding activity at pH 7.4≤ 3.0-fold as compared to the wild type ibalizumab (pH 7.4, 6.0 and 5.0 (left to right at each residue)). For each residue the rightmost column is "Fold reduced binding vs wt pH 5.0/Fold reduced binding vs wt pH 7.4." The Y-axis is "Fold reduced binding vs wt pH 5/Fold reduced binding vs wt pH 7."

For the light chain, the changes of the CD4-binding activity at pH 5.0, 6.0 and 7.4 with the mutations at different residues ("LCDR His variants") were given in FIG. 2A, and 10 LCDR residues when mutated to histidine were found to exhibit ≥ 50% less CD4-binding activity at pH 5.0 relative to pH 7.4 (pH 5.0/pH 7.4>1.5). Of these LCDR His variants, only 7 variants with a histidine mutation at the residue S26, L30, L33, Q89, Y92, S93 or Y94, which maintained CD4-binding activity at pH 7.4≤ 3.0-fold as compared to the wild type, as shown in FIG. 2B.

The CDR residues that mediate pH-dependent binding upon mutation to histidine were significantly found flanking residues critical for high affinity antigen-binding (P=x). For the VH, Y53a, D58 and T100a immediately flank residues that when mutated to histidine, had no detectable competition at maximum concentration tested (3 µg/mL), representing >32-fold loss in affinity. In addition, the pH-dependent K96/D97/N98 motif was flanked by E95 and Y99, which when mutated to histidine result in 7.5- and >32-fold loss in affinity, respectively. Similarly, for the VL, residues immediately flanking S26, L30 (flanked on both sides) and L33 resulted in >32-fold loss in affinity when mutated to His. Q90, flanking Q89 resulted in 21-fold reduced CD4-binding and Y91 and R95, flanking the Y92/S93/Y94 motif, resulted in 22-fold and 9-fold reduced CD4-binding at pH 7.4.

Example 2

Figure 3A:
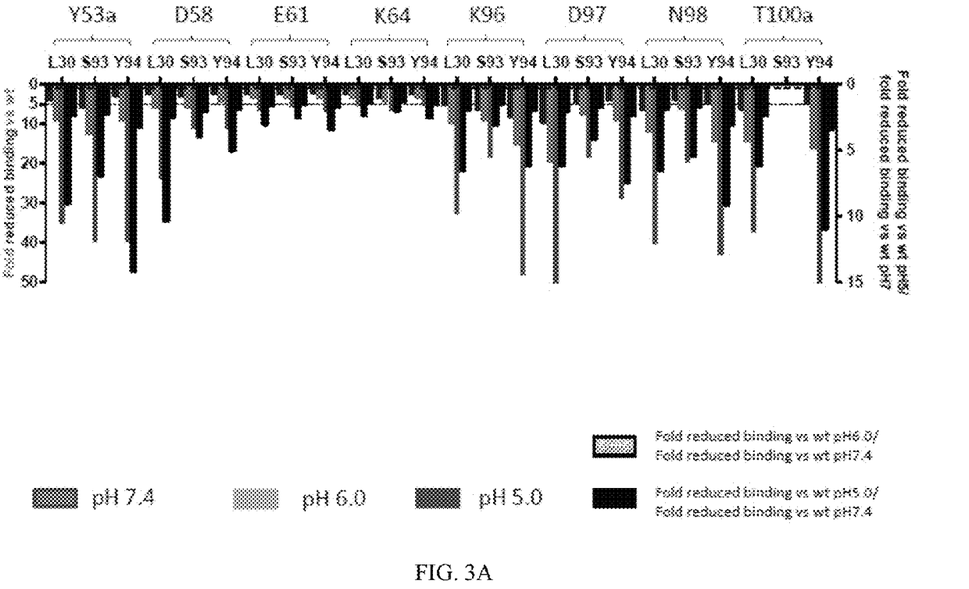
FIG. 3A shows the CD4-binding activity of the combination of a histidine mutation at the residue D58, E61, K64, K96, D97, N98 or T100a in the heavy chain of ibalizumab with any mutation at the residue L30, Y92, S93 or Y94 in the light chain of ibalizumab, demonstrating that the combination of the histidine mutations at the residues Y53a and Y94 ("Y53a/Y94") or the combination of the histidine mutations at the residues D58 and L30 ("D58/L30") of ibalizumab maintained the CD4-binding activity at pH 7.4≤ 3.0-fold as compared to the wild type ibalizumab (pH 7.4, 6.0, 5.0, "Fold reduced binding vs wt pH 5.0/Fold reduced binding vs wt pH 7.4." and "Fold reduced binding vs wt pH 6.0/Fold reduced binding vs wt pH 7.4" (left to right at each residue)).
Figure 3B:
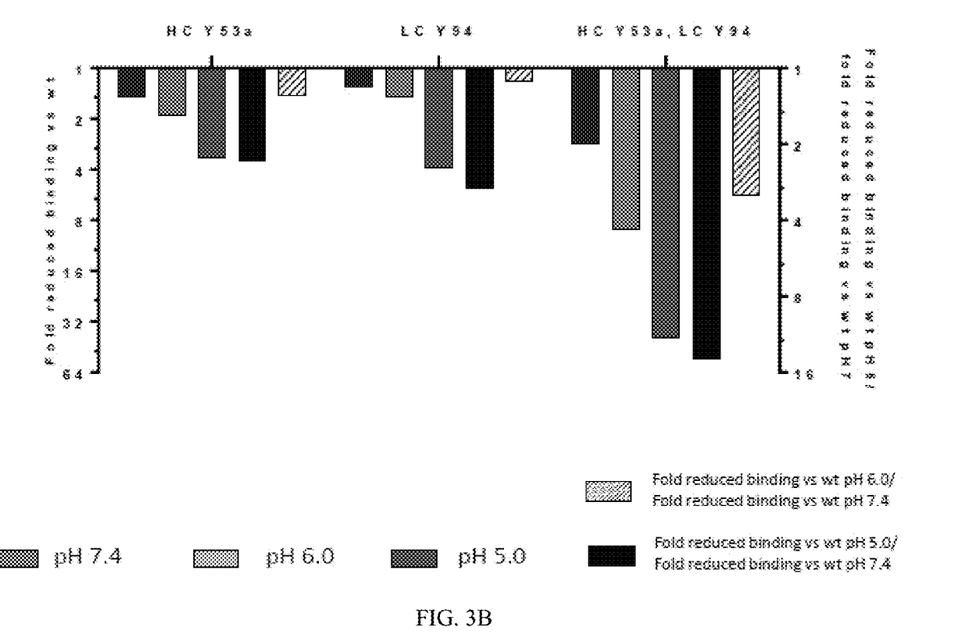
FIG. 3B shows the CD4-binding activity of the combination variant HC Y53a/LC Y94, as compared to that of the variants with a single mutation of Y53a or Y94 in the light chain of ibalizumab (pH 7.4, 6.0, 5.0, "Fold reduced binding vs wt pH 5.0/Fold reduced binding vs wt pH 7.4." and "Fold reduced binding vs wt pH 6.0/Fold reduced binding vs wt pH 7.4" (left to right at each residue)).

Identification of Optimal Histidine Combinations for Mediating pH-Dependent CD4-Binding Activity To determine whether a combination of a histidine mutation at the residue Y53a, D58, K96, D97, N98 or T100a as well as E61 and K64 in the heavy chain would improve pH-dependent CD4-binding, we assessed the effect of combining up to 4 light chain mutations in a single construct using the 4 light chain mutations that yielded the greatest pH-dependent CD4-binding activity (L30, Y92, S93 and Y94). As shown in FIG. 3, the combination of S93 and Y94, which individually yielded a pH 5.0/pH 7.4 differential of 1.5, resulted in a pH 5.0/pH 7.4 differential of 3.0. The addition of Y92, which alone produced a pH 5.0/pH 7.4 differential of 1.7, to the S93/Y94 double mutant, improved the pH 5.0/pH 7.4 differential to 3.4 and likewise, the addition of the L30 mutation, which alone produced a pH 5.0/pH 7.4 differential of 1.4, to the triple Y92H/S93H/Y94H variant further improved the pH 5.0/pH 7.4 differential to 5.7. Therefore, combining histidine mutations that individually mediate pH-dependent CD4-binding activity into a single molecule mediated greater pH-dependency. Unfortunately, however, combining multiple histidine mutations had detrimental effects on CD4-binding activity at pH 7.4. Indeed, the loss of binding affinity of combination variants was substantially greater than the sum of the individual variants. Linear regression of the observed loss of binding affinity of the combination variants fit better to the expected loss of binding based on multiplicative (P=0.0008) versus additive (P=0.06) effects of the individual mutations (sec FIG. 3). Therefore, in order to maintain sufficient CD4-binding affinity at pH 7.4, we focused on identifying optimal combinations of single VH and single VL histidine mutations.

To identify optimal combinations of single VH and single VL histidine mutations, we co-expressed each of the VH and VL pH-dependent antigen binding mutations in pairwise combinations and determined their ph-dependency by competition ELISA. Due to the greater loss of affinity for CD4 at pH 7.4 of combination His variants and our desire to preserve CD4-binding affinity at pH 7.4 as much as possible, we omitted VL mutants S26, S28, Q89 and Y92 since their magnitude of pH-dependence, even at pH 5.0 (pH 5.0/pH 7.4≤ 2.6) was less than their loss of affinity at pH 7.4 (>2.6-fold vs wt). We also included VH His mutants E61 and K64, which strictly maintained CD4 affinity at pH 7.4 (1.4-fold and 0.9-fold vs wt, respectively) and exhibited minor pH-dependence (pH 5.0/pH 7.4=1.6) as controls. As shown in FIG. 3A, HC/LC combination variants of Y94H exhibited significantly greater pH-dependence (pH 6.0/pH 7.4=2.4+0.7) than HC/LC combination variants of S93 (pH6.0/pH 7.4=1.7+0.3, P=0.04), with HC/LC combination variants of L30 mediating moderate pH-dependence (pH 6.0/pH 7.4=2.0+0.4), consistent with their rank order in the previous results. Furthermore, the 6 control HC/LC combination variants of E61 and K64 ranked in the bottom 7 for pH-dependence (pH 5.0/pH7.4), also consistent with the previous results.

The HC Y53a/LC Y94 combination variant exhibited the greatest pH-dependence, with 40-fold and 9-fold lower affinity at pH 5.0 and pH 6.0, respectively compared to the wt, while exhibiting only 2.4-fold lower affinity than wt at pH 7.4, resulting in pH 5.0/pH 7.4 and pH 6.0/pH7.4 differentials of 14.1 and 3.2, respectively. Importantly, the HC Y53a/LC Y94 combination variant exhibits appreciable pH-dependence at the more physiologically relevant pH 6.0 (pH 6.0/pH 7.4=3.2). As shown in FIG. 3B, this was not evident in the single Y53a (pH 6.0/pH 7.4=1.3) nor Y94 (pH 6.0/pH 7.4=1.1) variants for whom pH-dependence was only observed at pH 5.0 (pH 5.0/pH 7.4=2.3 and 3.0, respectively), validating the approach of using PH 5.0 for improving sensitivity during screening of single histidine mutants for pH-dependent binding. Indeed, the double mutant exhibits slightly greater pH-dependent binding at pH 6.0 (pH 6.0/pH 7.4=3.2) than either mutant at pH 5.0 (pH 5.0/pH 7.4=2.3 and 3.0).

Example 3

Confirmation of pH-Dependent CD4-Binding Activity by Surface Plasmon Resonance

Binding affinity analyses were performed with a BIA-CORE T3000 optical biosensor (GE Healthcare, Piscataway, N.J.). Immobilization of ibalizumab and all the variants were performed following the standard procedure.

Briefly, carboxyl groups on the sensor chip surface were activated by injection of 35 μL of a solution containing 0.2 M N-(3-dimethylaminopropyl)-N-ethylcarbodiimide and 0.05 M Nhydroxysuccinimide at a flow rate of 5 μL/minute. Next, ibalizumab or its mutant variant, at a concentration of 2 μg/mL in 10 mM sodium-acetate buffer, pH 4.5, was allowed to flow over the chip surface at a rate of 10 μL/minute until the desired level of response units of reacted protein (150-200 RU) was achieved. After unreacted protein was washed out, excess active ester groups on the sensor surface were capped by the injection of 35 μL of 1 M ethanolamine, pH 8.0, at a flow rate of 5 μL/minute. As background to correct instrument and buffer artifacts, a reference was generated under the same conditions with omission of the protein ligand. Binding experiments were performed at 25° C. in HBS-EP buffer (0.01 M HEPES, 0.15M NaCl, 3 mM EDTA, 0.005% vol/vol surfactant P20 (GE Healthcare). Binding kinetics were measured by passing various concentrations of analyte (human CD4 protein) over the chip surface at a flow rate of 30 μL/minute for 3 min. Dissociation of bound analytes was monitored while the surface was washed for 10 min. Remaining analytes were removed at a flow rate of 50 μL/minute with two 30-sec injections of 10 mM glycine-HCl, pH 2.0. For kinetics data analysis, the kinetic parameters were determined by collectively fitting the overlaid sensograms locally using the BIAevaluation 4.1 software to the 1:1 Langmuir binding model.

We examined the binding kinetics of the lead histidine variant, Y53aH/Y94H identified from the competition ELISA screening assay, using surface plasmon resonance (Biacore). As controls, we included wild type, the LC S56H variant, which did not exhibit pH-dependency (pH 5.0/pH 7.4=0.8) and maintained affinity at pH 7.4 (1.3-fold vs wt) and the HC D97/LC S93, Y94 variant which exhibited pH-dependent CD4-binding activity but also, lost substantial binding at pH 7.4.

As shown in FIG. 5, the in vitro HIV-1 neutralization activity of the wild type ibalizumab (MV1-LALA) is similar to that of the variant HC Y53a/LC Y94, including Y94/Y53a-LALA and Y94/Y53a-LALA FcRn, wherein the isotype control (h4G7) was included.

Example 4

Pharmacokinetics Analysis

The pharmacokinetics of wild type ibalizumab (Wt, blue lines) and the variant HC Y53a/LC Y94 (His, green lines and His FcRn, red lines) in Rhesus macaques were shown in FIG. 6A. As shown in FIG. 6B, the duration of CD4 occupancy by the wild type ibalizumab (Wt, blue lines) and the variant HC Y53a/LC Y94 (His, green lines and His FcRn, red lines) in Rhesus macaques administered the respective antibody at 0.75 mg/kg. Each line, indicating the CD4 occupancy observed in an individual rhesus macaque.

Example 6

Analysis for Down Modulation

Figure 7:
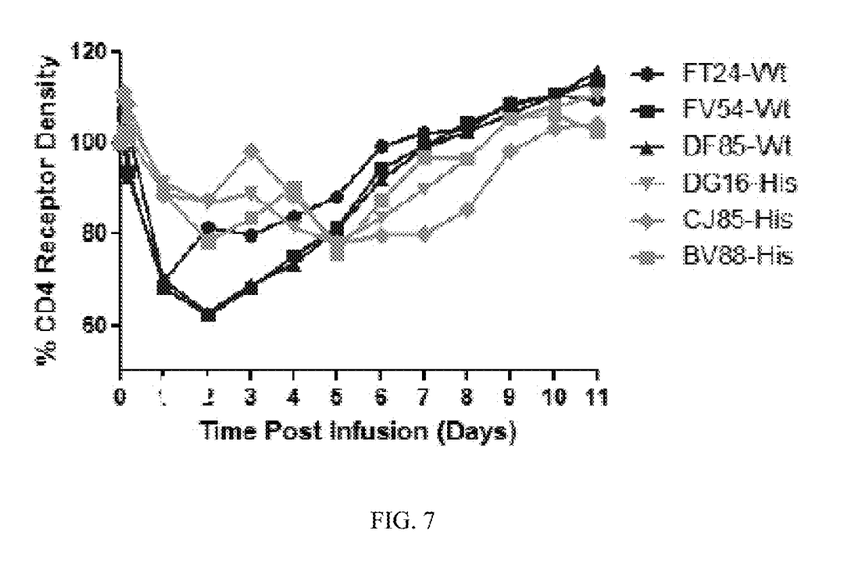
FIG. 7 shows that the histidine variant induced a lesser degree of CD4 receptor down modulation than the wild type ibalizumab.

As shown in FIG. 7, the histidine mutated variants of ibalizumab induced a lesser degree of CD4 receptor down modulation than the wild type ibalizumab.

While the present invention has been disclosed by way of preferred embodiments, it is not intended to limit the present invention. Any person of ordinary skill in the art may, without departing from the spirit and scope of the present invention, shall be allowed to perform modification and embellishment. Therefore, the scope of protection of the present invention shall be governed by which defined by the claims attached subsequently.

SEQUENCE LISTING

SEQ ID NO: 1: the amino acid sequence of the human CD4 receptor (amino acids 1-25 representing a signal peptide, amino acids 26-122 constituting D1, and amino acids 123-205 constituting D2):

MNRGVPFRHLLLLVLQLALLPAATQGKKVVLGKKGDTVELTCTASQKKS

IQFHWKNSNQIKILGNQGSFLTKGPSKLNDRADSRRSLWDQGNFPLIIK

NLKIEDSDTYICEVEDQKEEVQLLVFGLTANSDTHLLQGQSLTLTLESP

PGSSPSVQCRSPRGKNIQGGKTLSVSQLELQDSGTWTCTVLQNQKKVEF

KIDIVVLAFQKASSIVYKKEGEQVEFSFPLAFTVEKLTGSGELWWQAER

ASSSKSWITFDLKNKEVSVKRVTQDPKLQMGKKLPLHLTLPQALPQYAG

SGNLTLALEAKTGKLHQEVNLVVMRATQLQKNLTCEVWGPTSPKLMLSL

KLENKEAKVSKREKAVWVLNPEAGMWQCLLSDSGQVLLESNIKVLPTWS

TPVQPMALIVLGGVAGLLLFIGLGIFFCVRCRHRRRQAERMSQIKRLLS

EKKTCQCPHRFQKTCSPI

SEQ ID NO: 2: the amino acid sequence of the heavy chain of MV1 (471 amino acids, including the first 19 amino acid residues constituting a leader sequence):

MEWSGVFMFLLSVTAGVHSQVQLQQSGPEVVKPGASVKMSCKASGYTFT

SYVIHWVRQKPGQGLDWIGYINPYNDGTDYDEKFKGKATLTSDTSTSTA

YMELSSLRSEDTAVYYCAREKDNYATGAWFAYWGQGTLVTVSSASTKGP

SVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCD

KTHTCPPCPAPEFEGGPSVFLEPPKPKDTLMISRTPEVTCVVVDVSHED

PEVKFNWYVDGVEVHNAKTKPREEQYNSTYRVVSVLTVLHQDWLNGKEY

KCKVSNKALPASIEKTISKAKGQPREPQVYTLPPSRDELTKNQVSLTCL

VKGFYPSDIAVEWESNGQPENNYKTTPPVLDSDGSFFLYSKLTVDKSRW

QQGNVFSCSVMHEALHNHYTQKSLSLSPGK*

SEQ ID NO: 3: the amino acid sequence of the light chain of MV1 (238 amino acids, including the first 19 amino acids which constitute a leader sequence):

MEWSGVFIFL LSVTAGVHSD IVMTQSPDSL AVSLGERVTM

NCKSSQSLLY STNQKNYLAW YQQKPGQSPK LLIYWASTRE

SGVPDRFSGS GSGTDFTLTI SSVQAEDVAV YYCQQYYSYR

TFGGGTKLEI KRTVAAPSVF IFPPSDEQLK SGTASVVCLL

NNFYPREAKV QWKVDNALQS GNSQESVTEQ DSKDSTYSLS

STLTLSKADY EKHKVYACEV THQGLSSPVT KSFNRGEC

SEQ ID NO: 4: the amino acid sequence of the Light chain of LM52:

DIVMTQSPDSLAVSLGERVTMNCKSSQSLLYSTNQKNYLAWYQQKPGQS
PKLLIYWANSTESGVPDRFSGSGSGTDFTLTISSVQAEDVAVYYCQQYY
SYRTFGGGTKLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSFNRGEC

---

What is claimed is:

1. A histidine-mutated anti-HIV antibody having one or more of the following mutations in the heavy chain of ibalizumab (amino acids 20-471 of SEQ ID NO: 2): Y73H, D78H, K119H, D120H, N121H, and T124H, or one or more of the following mutations in the light chain of ibalizumab (amino acids 20-238 of SEQ ID NO: 3): S45H, L49H, L58H, Q114H, Y117H, S118H, and Y119H; wherein the ibalizumab is comprises in its light chain an engineered N-linked glycosylation site at the amino acid position selected from the group consisting of positions 54Gln, 77Ser, 78Thr, 79Arg, 85Asp, 90Ser, 92Ser, and 101Ser; wherein the antibody has a pH-dependent CD4-binding activity.

2. The histidine-mutated anti-HIV antibody of claim 1, which has a combination of the mutations at the residues in the heavy and light chains of ibalizumab respectively, wherein the residue(s) is (are) selected from the group consisting of Y73H, D78H, K119H, D120H, N121H, and T124H and a combination thereof, and the mutation at one of the residues in the light chain of said antibody selected from the group consisting of S45H, L49H, L58H, Q114H, Y117H, S118H, and Y119H S26, L30, L33, Q89, Y92, S93, Y94 and a combination thereof.

3. The histidine-mutated anti-HIV antibody of claim 1, which has a combination of the mutation at the residue of Y73H Y53a in the heavy chain of ibalizumab, and the mutation at one of the residues in the light chain of ibalizumab selected from the group consisting of S45H, L49H, L58H, Q114H, Y117H, S118H, and Y119H and a combination thereof.

4. The histidine-mutated anti-HIV antibody of claim 1, which has a combination of the mutation of D78H D58 in the heavy chain of ibalizumab, and the mutation at one of the residues in the light chain of ibalizumab selected from the group consisting of S45H, L49H, L58H, Q114H, Y117H, S118H, and Y119H and a combination thereof.

5. A histidine-mutated anti-HIV antibody, which is a variant with two histidine mutations at the residues Y73in the heavy chain, and Y119in the light chain of ibalizumab, respectively, and wherein the ibalizumab comprises in its light chain an engineered N-linked glycosylation site at the amino acid position selected from the group consisting of positions 54Gln, 77Ser, 78Thr, 79Arg, 85Asp, 90Ser, 92Ser, and 101Ser.

6. A histidine-mutated anti-HIV antibody, which is a variant with two histidine mutations at the residues D78in the heavy chain, and L49in the light chain of ibalizumab, respectively; and wherein the ibalizumab is modified by comprises in its light chain an engineered N-linked glycosylation at the amino acid position selected from the group consisting of positions 54Gln, 77Ser, 78Thr, 79Arg, 85Asp, 90Ser, 92Ser, and 101Ser.

7. A pharmaceutical composition comprising the antibody set forth in claim 1 and at least one pharmaceutically acceptable carrier.

8. A method of treating a subject infected with HIV comprising administering to the subject a therapeutically effective amount of the antibody set forth in claim 1.

9. A method of preventing HIV infection in a subject in need thereof comprising administering to the subject a therapeutically effective amount of the antibody set forth in any one of claim 1.

10. A pharmaceutical composition comprising the antibody set forth in claim 5 and at least one pharmaceutically acceptable carrier.

11. A method of treating a subject infected with HIV comprising administering to the subject a therapeutically effective amount of the antibody set forth in claim 5.

12. A method of preventing HIV infection in a subject in need thereof comprising administering to the subject a therapeutically effective amount of the antibody set forth in any one of claim 5.

13. A pharmaceutical composition comprising the antibody set forth in claim 6 and at least one pharmaceutically acceptable carrier.

14. A method of treating a subject infected with HIV comprising administering to the subject a therapeutically effective amount of the antibody set forth in claim 6.

15. A method of preventing HIV infection in a subject in need thereof comprising administering to the subject a therapeutically effective amount of the antibody set forth in any one of claim 6.

16. The histidine-mutated anti-HIV antibody of claim 1, which has a lower CD4-binding affinity at pH 5.0 or pH 6.0 than that at pH 7.4.

* * * * *

SEQUENCE LISTING

<160> NUMBER OF SEQ ID NOS: 4

<210> SEQ ID NO 1
<211> LENGTH: 459
<212> TYPE: PRT
<213> ORGANISM: Homo sapiens

<400> SEQUENCE: 1

Met Asn Arg Gly Val Pro Phe Arg His Leu Leu Leu Val Leu Gln
1               5                   10                  15

Leu Ala Leu Leu Pro Ala Ala Thr Gln Gly Lys Lys Val Leu Gly
                20                  25                  30

Lys Lys Gly Asp Thr Val Glu Leu Thr Cys Thr Ala Ser Gln Lys Lys
                35                  40                  45

Ser Ile Gln Phe His Trp Lys Asn Ser Asn Gln Ile Lys Ile Leu Gly
                50                  55                  60

Asn Gln Gly Ser Phe Leu Thr Lys Gly Pro Ser Lys Leu Asn Asp Arg
65                  70                  75                  80

Ala Asp Ser Arg Arg Ser Leu Trp Asp Gln Gly Asn Phe Pro Leu Ile
                85                  90                  95

Ile Lys Asn Leu Lys Ile Glu Asp Ser Asp Thr Tyr Ile Cys Glu Val
                100                 105                 110

Glu Asp Gln Lys Glu Glu Val Gln Leu Leu Val Phe Gly Leu Thr Ala
                115                 120                 125

Asn Ser Asp Thr His Leu Leu Gln Gly Gln Ser Leu Thr Leu Thr Leu
                130                 135                 140

Glu Ser Pro Pro Gly Ser Ser Pro Ser Val Gln Cys Arg Ser Pro Arg
145                 150                 155                 160

Gly Lys Asn Ile Gln Gly Gly Lys Thr Leu Ser Val Ser Gln Leu Glu
                165                 170                 175

Leu Gln Asp Ser Gly Thr Trp Thr Cys Thr Val Leu Gln Asn Gln Lys
                180                 185                 190

Lys Val Glu Phe Lys Ile Asp Ile Val Val Leu Ala Phe Gln Lys Ala
                195                 200                 205

Ser Ser Ile Val Tyr Lys Lys Glu Gly Glu Gln Val Glu Phe Ser Phe
                210                 215                 220

Pro Leu Ala Phe Thr Val Glu Lys Leu Thr Gly Ser Gly Glu Leu Trp
225                 230                 235                 240

Trp Gln Ala Glu Arg Ala Ser Ser Ser Lys Ser Trp Ile Thr Phe Asp
                245                 250                 255

Leu Lys Asn Lys Glu Val Ser Val Lys Arg Val Thr Gln Asp Pro Lys
                260                 265                 270

Leu Gln Met Gly Lys Lys Leu Pro Leu His Leu Thr Leu Pro Gln Ala
                275                 280                 285

Leu Pro Gln Tyr Ala Gly Ser Gly Asn Leu Thr Leu Ala Leu Glu Ala
                290                 295                 300

Lys Thr Gly Lys Leu His Gln Glu Val Asn Leu Val Val Met Arg Ala
305                 310                 315                 320

```
Thr Gln Leu Gln Lys Asn Leu Thr Cys Glu Val Trp Gly Pro Thr Ser
            325                 330                 335

Pro Lys Leu Met Leu Ser Leu Lys Leu Glu Asn Lys Glu Ala Lys Val
            340                 345                 350

Ser Lys Arg Glu Lys Ala Val Trp Val Leu Asn Pro Glu Ala Gly Met
            355                 360                 365

Trp Gln Cys Leu Leu Ser Asp Ser Gly Gln Val Leu Leu Glu Ser Asn
            370                 375                 380

Ile Lys Val Leu Pro Thr Trp Ser Thr Pro Val Gln Pro Met Ala Leu
385                 390                 395                 400

Ile Val Leu Gly Gly Val Ala Gly Leu Leu Leu Phe Ile Gly Leu Gly
            405                 410                 415

Ile Phe Phe Cys Val Arg Cys Arg His Arg Arg Arg Gln Ala Glu Arg
            420                 425                 430

Met Ser Gln Ile Lys Arg Leu Leu Ser Glu Lys Lys Thr Cys Gln Cys
            435                 440                 445

Pro His Arg Phe Gln Lys Thr Cys Ser Pro Ile
            450                 455

<210> SEQ ID NO 2
<211> LENGTH: 471
<212> TYPE: PRT
<213> ORGANISM: Homo sapiens

<400> SEQUENCE: 2

Met Glu Trp Ser Gly Val Phe Met Phe Leu Leu Ser Val Thr Ala Gly
1               5                   10                  15

Val His Ser Gln Val Gln Leu Gln Gln Ser Gly Pro Glu Val Val Lys
            20                  25                  30

Pro Gly Ala Ser Val Lys Met Ser Cys Lys Ala Ser Gly Tyr Thr Phe
            35                  40                  45

Thr Ser Tyr Val Ile His Trp Val Arg Gln Lys Pro Gly Gln Gly Leu
        50                  55                  60

Asp Trp Ile Gly Tyr Ile Asn Pro Tyr Asn Asp Gly Thr Asp Tyr Asp
65                  70                  75                  80

Glu Lys Phe Lys Gly Lys Ala Thr Leu Thr Ser Asp Thr Ser Thr Ser
            85                  90                  95

Thr Ala Tyr Met Glu Leu Ser Ser Leu Arg Ser Glu Asp Thr Ala Val
            100                 105                 110

Tyr Tyr Cys Ala Arg Glu Lys Asp Asn Tyr Ala Thr Gly Ala Trp Phe
            115                 120                 125

Ala Tyr Trp Gly Gln Gly Thr Leu Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
            165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Lys Val Glu
```

```
                225                 230                 235                 240
Pro Lys Ser Cys Asp Lys Thr His Thr Cys Pro Pro Cys Pro Ala Pro
                    245                 250                 255

Glu Phe Glu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                        325                 330                 335

Trp Leu Asn Gly Lys Glu Tyr Lys Cys Lys Val Ser Asn Lys Ala Leu
                340                 345                 350

Pro Ala Ser Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                        405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 3
<211> LENGTH: 238
<212> TYPE: PRT
<213> ORGANISM: Homo sapiens

<400> SEQUENCE: 3

Met Glu Trp Ser Gly Val Phe Ile Phe Leu Leu Ser Val Thr Ala Gly
1               5                   10                  15

Val His Ser Asp Ile Val Met Thr Gln Ser Pro Asp Ser Leu Ala Val
                20                  25                  30

Ser Leu Gly Glu Arg Val Thr Met Asn Cys Lys Ser Ser Gln Ser Leu
            35                  40                  45

Leu Tyr Ser Thr Asn Gln Lys Asn Tyr Leu Ala Trp Tyr Gln Gln Lys
        50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Val Tyr Tyr
                100                 105                 110

Cys Gln Gln Tyr Tyr Ser Tyr Arg Thr Phe Gly Gly Gly Thr Lys Leu
            115                 120                 125
```

```
Glu Ile Lys Arg Thr Val Ala Ala Pro Ser Val Phe Ile Phe Pro Pro
            130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                    165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
195                 200                 205

Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys
225                 230                 235
```

<210> SEQ ID NO 4
<211> LENGTH: 219
<212> TYPE: PRT
<213> ORGANISM: Homo sapiens

<400> SEQUENCE: 4

```
Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Leu Leu Tyr Ser
                20                  25                  30

Thr Asn Gln Lys Asn Tyr Leu Ala Trp Tyr Gln Gln Lys Pro Gly Gln
            35                  40                  45

Ser Pro Lys Leu Leu Ile Tyr Trp Ala Asn Ser Thr Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

UNITED STATES PATENT AND TRADEMARK OFFICE
CERTIFICATE OF CORRECTION

| | | |
|---|---|---|
| PATENT NO. | : 12,012,451 B2 | Page 1 of 1 |
| APPLICATION NO. | : 16/997547 | |
| DATED | : June 18, 2024 | |
| INVENTOR(S) | : Craig Stuart Pace et al. | |

It is certified that error appears in the above-identified patent and that said Letters Patent is hereby corrected as shown below:

In the Claims

Column 23, Claim 1, Line 9, replace "is comprises" with --comprises--;
    Claim 2, Lines 23-24, replace "Y119H S26, L30, L33, Q89, Y92, S93, Y94" with --Y119H--;
    Claim 3, Line 26, replace "the mutation at the residue of Y73H Y53a" with --the mutation of Y73H--;
    Claim 4, Line 33, replace "D78H D58" with --D78H--;
    Claim 5, Line 39, replace "Y73in" with --Y73 in--;
        Line 40, replace "Y119in" with --Y119 in--.

Column 24, Claim 6, Line 2, replace "D78in" with --D78 in--;
    Line 3, replace "L49in" with --L49 in--;
    Line 4, replace "ibalizumab is modified by" with --ibalizumab--.

Signed and Sealed this
Seventeenth Day of September, 2024

Katherine Kelly Vidal
*Director of the United States Patent and Trademark Office*